(12) United States Patent
Tao et al.

(10) Patent No.: US 8,222,596 B2
(45) Date of Patent: Jul. 17, 2012

(54) ANALYZER CONSTITUTED BY GAS CHROMATOGRAPH COMBINED WITH INDUCTIVELY COUPLED PLASMA MASS SPECTROMETER

(75) Inventors: Hiroaki Tao, Tsukuba (JP); Tetsuya Nakazato, Tsukuba (JP)

(73) Assignee: National Institue of Advanced Industrial Science and Technology, Tokyo (JP)

( * ) Notice: Subject to any disclaimer, the term of this patent is extended or adjusted under 35 U.S.C. 154(b) by 1317 days.

(21) Appl. No.: 11/850,194

(22) Filed: Sep. 5, 2007

(65) Prior Publication Data

US 2012/0126113 A1    May 24, 2012

(30) Foreign Application Priority Data

Sep. 5, 2006 (JP) .................................. 2006-239897
Aug. 20, 2007 (JP) .................................. 2007-213260

(51) Int. Cl.
*H01J 49/10* (2006.01)

(52) U.S. Cl. .................... 250/288; 250/281; 250/282

(58) Field of Classification Search .................. 250/281, 250/282, 288; 95/82, 85, 87, 88, 89; 96/101, 96/102, 104, 106

See application file for complete search history.

(56) References Cited

U.S. PATENT DOCUMENTS

| 5,345,079 | A   | * | 9/1994  | French et al.    | 250/288  |
|-----------|-----|---|---------|------------------|----------|
| 2003/0013199 | A1 | * | 1/2003  | Anderson et al.  | 436/50   |
| 2005/0235757 | A1 | * | 10/2005 | De Jonge et al.  | 73/861.07 |
| 2007/0151857 | A1 | * | 7/2007  | Farrusseng et al. | 204/639 |

FOREIGN PATENT DOCUMENTS

| JP | 2931967 B  | 5/1999  |
|----|------------|---------|
| JP | 2002-350402 | 12/2002 |
| JP | 2004-158314 | 6/2004  |
| JP | 2006-38729 | 2/2006  |

OTHER PUBLICATIONS

Jon C. Van Loon, et al., "Inductively Coupled, Plasma Source Mass Spectrometry—A New Element/Isotope Specific Mass Spectrometry Detector for Chromatography," Spectroscopy Letters, 19 (10), pp. 1125-1135, 1986.

N.S. Chong, et al., "Inductively Coupled Plasma-Mass Spectrometry for Elemental Analysis and Isotope Ratio Determinations in Individual Organic Compounds Separated by Gas Chromatography," Applied Spectroscopy, vol. 41, No. 1, pp. 66-74, 1987.

Stefan M. Gallus, et al., "Development of a Gas Chromatography Inductively Coupled Plasma Isotope Dilution Mass Spectrometry System for Accurate Determination of Volatile Element Species, Part 1. Selenium Speciation," Journal of Analytical Atomic Spectrometry, vol. 11 pp. 887-892 Sep. 1996.

* cited by examiner

*Primary Examiner* — David A Vanore
*Assistant Examiner* — Nicole Ippolito
(74) *Attorney, Agent, or Firm* — Law Office of Katsuhiro Arai

(57) ABSTRACT

The invention provides a new GC/ICP-MS capable of preventing carbon deposition caused by the analysis sample or its solvent. With a GC/ICP-MS, it is effective to introduce oxygen continuously or during a specific period to the part where argon or other makeup gas is introduced to the ICP-MS, and this is achieved by introducing oxygen in air into the gas supply line using an oxygen permeable tube or oxygen permeable membrane. A selector valve is used to introduce permeated oxygen to the aforementioned gas supply line only during a desired period.

22 Claims, 5 Drawing Sheets

27

26

ANALYZER CONSTITUTED BY GAS CHROMATOGRAPH COMBINED WITH INDUCTIVELY COUPLED PLASMA MASS SPECTROMETER

BACKGROUND OF THE INVENTION

1. Field of the Invention

The present invention relates to an analyzer constituted by gas chromatograph combined with inductively coupled plasma mass spectrometer.

2. Description of the Related Art

An analyzer constituted by gas chromatograph combined with inductively coupled plasma mass spectrometer (the gas chromatograph may also be referred to hereinafter as "GC," the inductively coupled plasma mass spectrometer as "ICP-MS," and the analyzer constituted by gas chromatograph combined with inductively coupled plasma mass spectrometer as "GC/ICP-MS") is used with appreciation as an analysis system (Patent Literature 1, Patent Literature 2, Patent Literature 3, and Patent Literature 4).

The target component of analysis is first introduced to the GC in a state dissolved in an organic solvent. Hexane, toluene and other hydrocarbon-based organic solvents are generally used as this organic solvent. The organic solvent is thermally decomposed in argon plasma inside the ICP-MS to become carbon, which then deposits around the orifices of the sampling cone and skimmer cone of the ICP-MS. This presents a problem because the orifice diameters are gradually reduced and the analysis sensitivity drops as a result.

Traditionally, carbon deposition caused by the above reason has been suppressed by a method where oxygen supplied from an oxygen cylinder is constantly introduced through a makeup gas supply line (Non-patent Literature 1), or another method where the ICP torch position is moved away from the sampling cone after a specific number of analysis sessions and air is introduced to ICP to burn, by means of oxygen in air, the carbon deposited around the orifices (Non-patent Literature 2).

However, the methods described in Patent Literatures 1 to 4 above cannot prevent carbon deposition, while the method described in Non-patent Literature 1 requires additional equipment such as an oxygen cylinder, oxygen gas supply line, flow rate controller and mixer, thus making the system complex. The method described in Non-patent Literature 2 requires no additional equipment, but it makes the operation cumbersome and the analysis accuracy also drops because the torch position is moved. All of these GC/ICP-MS apparatuses have been unable to effectively prevent carbon deposition caused by the analysis sample.

[Patent Literature 1] Japanese Patent No. 2931967
[Patent Literature 2] Japanese Patent Laid Open No. 2002-350402
[Patent Literature 3] Japanese Patent Laid Open No. 2004-158314
[Patent Literature 4] Japanese Patent Laid Open No. 2006-38729
[Non-patent Literature 1] J. C. Van Loon, L. R. Alcock, W. H. Pinchin, J. B. French: *Spectroscopy Letters*, 19 (10), 1125-1135 (1986). Description in Abstract: "Oxygen gas (about 20% of the total sample gas flow) must be injected, into the GC effluent entering the torch, to prevent carbon buildup on the torch."
[Non-patent Literature 2] N. S. Chong, R. S. Houk: *Applied Spectroscopy*, 41 (1), 66-74 (1987). Description on p. 67: "One could remove the carbon deposit by displacing the torch laterally to bring about spontaneous oxidation of carbon by air on the hot sampler cone."

SUMMARY OF THE INVENTION

A problem to be solved by an embodiment of the present invention is to provide a new GC/ICP-MS capable of preventing carbon deposition caused by the analysis sample or its solvent, by doing away with the inconveniences encountered with conventional apparatuses, or specifically without requiring an oxygen cylinder, oxygen gas supply line, flow rate controller or mixer, and without moving the torch position.

As a result of earnest study to solve the aforementioned problem, the inventors found that it was necessary to introduce oxygen continuously or during a specific period into the part through which argon or other makeup gas is introduced to the ICP-MS. Accordingly, the inventors constructed a structure comprising an oxygen permeable tube or oxygen permeable membrane in at least one part of the supply line of gas introduced to the inductively coupled plasma mass spectrometer or gas for generating plasma, so that oxygen in air can be taken in through the oxygen permeable tube or oxygen permeable membrane according to the difference in partial pressure of oxygen, thereby allowing the permeated oxygen to be introduced to the gas supply line to plasma. It was revealed that, as a result of this structure, oxygen can be introduced continuously or during a specific period into the existing gas supply line of the gas chromatograph/inductively coupled plasma mass spectrometer without requiring an oxygen cylinder, oxygen gas supply line, flow rate controller or mixer.

In other words, embodiments of the present invention are characterized by 1) to 7) specified below:

1) An analyzer constituted by gas chromatograph combined with inductively coupled plasma mass spectrometer, wherein the analyzer constituted by gas chromatograph combined with inductively coupled plasma mass spectrometer is characterized by having an oxygen permeable tube or oxygen permeable membrane in at least one part of the supply line of gas introduced to the inductively coupled plasma mass spectrometer or gas for generating plasma.

2) An analyzer constituted by gas chromatograph combined with inductively coupled plasma mass spectrometer according to 1), wherein the at least one part of the supply line of gas introduced to the inductively coupled plasma mass spectrometer or gas for generating plasma constitutes a part of the line before the connection point with the gas supply line leading from the outlet of the gas chromatograph.

3) An analyzer constituted by gas chromatograph combined with inductively coupled plasma mass spectrometer according to 1) or 2), wherein the at least one part of the supply line of gas introduced to the inductively coupled plasma mass spectrometer or gas for generating plasma constitutes a part of the line before the connection point with the gas supply line leading from the outlet of the gas chromatograph, and wherein this part of the line has a selector valve installed at the location connecting the front and rear sections of the line and having an oxygen permeable tube or oxygen permeable membrane, so that when the selector valve is switched, oxygen can be introduced during a desired period through the location having the oxygen permeable tube or oxygen permeable membrane.

4) An analyzer constituted by gas chromatograph combined with inductively coupled plasma mass spectrometer according to 3), wherein the analyzer comprises an automatic control unit that switches the selector valve using electrical signals.

5) An analyzer constituted by gas chromatograph combined with inductively coupled plasma mass spectrometer according to 4), wherein a trigger signal is output from the ICP-MS to the automatic control unit when the signal intensity attributable to the solvent exceeds a specific level, and a trigger signal is output again when the signal intensity drops to or below the specific level, and the selector valve is switched.

6) An analyzer constituted by gas chromatograph combined with inductively coupled plasma mass spectrometer according to any one of 1) to 5), wherein the oxygen permeable tube has a double-tube structure comprising an outer tube constituted by an oxygen permeable tube and an inner tube constituted by an oxygen impermeable tube.

7) An analyzer constituted by gas chromatograph combined with inductively coupled plasma mass spectrometer according to any one of 3) to (6), wherein a buffer for mitigating abrupt rise in the oxygen content of oxygen gas is provided in a part of the gas supply line between the selector valve and a plasma torch.

A gas chromatograph/inductively coupled plasma mass spectrometer (GC/ICP-MS) can be provided that allows oxygen to be introduced to a part of the supply line of gas introduced to plasma or gas for generating plasma, in order to prevent carbon from depositing around the orifices of the sampling cone and skimmer cone of the ICP-MS due to the organic solvent introduced to the GC simultaneously with the target component of analysis when the target component of analysis is introduced to inductively coupled plasma (ICP) in gaseous state, i.e., as gas molecules being output from the gas chromatograph (GC).

An embodiment of the present invention, which adopts a structure having an oxygen permeable tube or oxygen permeable membrane in at least one part of the supply line of gas introduced to the inductively coupled plasma mass spectrometer or gas for generating plasma, makes it possible to take in oxygen in air through the oxygen permeable tube or oxygen permeable membrane according to the difference in partial pressure of oxygen, thereby allowing the permeated oxygen to be introduced to the gas supply line to plasma. Introduced oxygen is carried to plasma and caused to react with the organic solvent released from the GC or with the solid carbon deposited on the sampling cone and skimmer cone, to become CO or $CO_2$. If oxygen is not supplied, the organic solvent remains as solid carbon on the sampling cone and skimmer cone for a prolonged period of time. Since the amount of this carbon increases with the number of analysis sessions, the sensitivity drops over time. If oxygen is supplied, the solid carbon deposited on the sampling cone and skimmer cone becomes gas such as CO or $CO_2$ and is removed over a short period of time. Therefore, the analysis sensitivity is maintained at a certain level. In addition, by using a selector valve to introduce oxygen to plasma only during the period in which the solvent is introduced to plasma, and a brief period thereafter, it becomes possible to not only suppress carbon deposition but also to carry out analysis without reducing the sensitivity to the target component of analysis because of oxygen. To be specific, while it has been reported (in Non-patent Literature 3, for example) that continuous introduction of oxygen can lead to a drop in sensitivity because the characteristics of generated plasma become different from those of near-100% argon plasma, it becomes possible to carry out analysis without reducing the sensitivity to the target component of analysis because of oxygen, if oxygen is introduced only during the period in which the solvent is introduced to plasma, and a brief period thereafter, while stopping the oxygen during the period in which the target component of analysis that has been separated from the solvent by the gas chromatograph is introduced to plasma. Even when the target component of analysis is one prone to oxygen interference (such as any sulfur compound), the component can be analyzed without oxygen interference by introducing oxygen only during the period in which the solvent is introduced to plasma, and a brief period thereafter, while stopping the oxygen during the period in which the target component of analysis that has been separated from the solvent by the gas chromatograph is introduced to plasma. As explained above, providing an oxygen permeable tube or oxygen permeable membrane in at least one part of the supply line of gas introduced to plasma or gas for generating plasma allows for suppression of carbon deposition on the sampling cone and skimmer cone without requiring an oxygen cylinder, oxygen gas supply line, flow rate controller or mixer. As a secondary effect, such gas chromatograph/inductively coupled plasma mass spectrometer can be tuned based on the signal intensity of oxygen ions ($O^+$) or molecular ions containing oxygen such as $CO^+$ and $ArO^+$, which eliminate the need of expensive Xe gas, unlike with current apparatuses where Xenon (Xe) gas or the like is introduced to perform tuning based on the signal intensity of $Xe^+$.

[Non-patent Literature 3] S. M. Gallus, K. G. Heumann: *Journal of Analytical Atomic Spectrometry*, 11, 887-892 (1996). Description on p. 889: "It was necessary to stop the $O_2$ gas flow . . . because a distinct depression of the selenium isotope intensities, by a factor of about three, was found under these conditions compared with use of a pure argon plasma gas"

For purposes of summarizing the invention and the advantages achieved over the related art, certain objects and advantages of the invention are described in this disclosure. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention. The drawings are oversimplified for illustrative purposes and are not to scale.

DESCRIPTION OF THE SYMBOLS

Figure 1A:
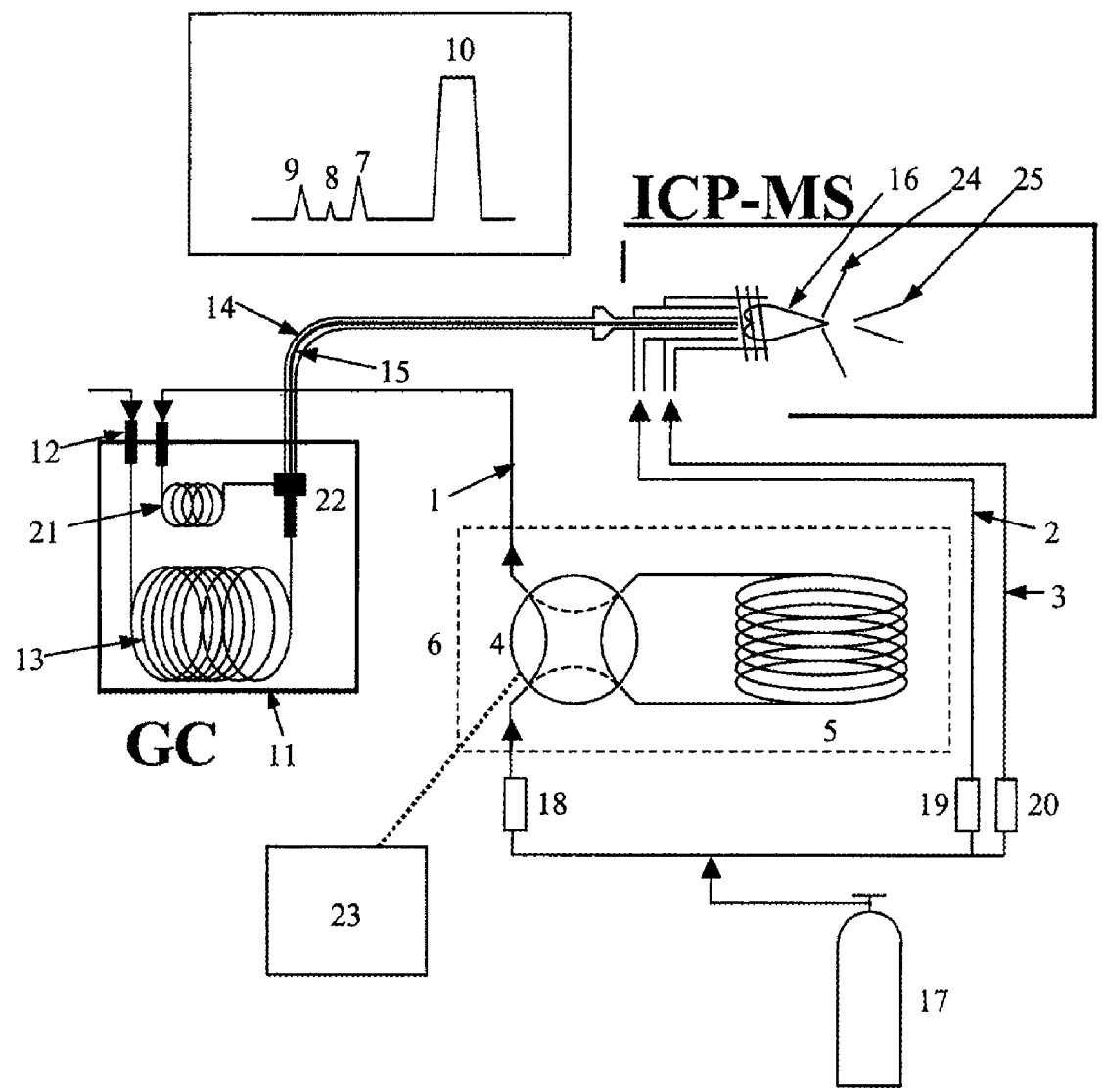
FIG. 1(a) is a drawing showing an embodiment of an analyzer constituted by gas chromatograph and inductively coupled plasma mass spectrometer conforming to the present invention.

1 Makeup gas supply line
2 Auxiliary gas supply line
3 Plasma gas supply line
4 Selector valve
5 Oxygen permeable tube
6 Oxygen introduction unit
7, 8, 9 Target component of analysis
10 Solvent
11 Gas chromatograph (GC)
12 Injection port
13 Column
14 Heating transfer tube
15 Inactivation column
16 Plasma (ICP)
17 Ar cylinder
18, 19, 20 Mass flow controller
21 Pre-heater
22 Connector
23 Automatic control unit
24 Sampling cone
25 Skimmer cone
26 Oxygen permeable membrane
27 Oxygen permeation module

DETAILED DESCRIPTION OF THE PREFERRED EMBODIMENT

An embodiment of the present invention provides an analyzer constituted by gas chromatograph combined with inductively coupled plasma mass spectrometer, wherein such analyzer constituted by gas chromatograph combined with inductively coupled plasma mass spectrometer is characterized by having an oxygen permeable tube or oxygen permeable membrane in at least one part of the supply line of gas introduced to the inductively coupled plasma mass spectrometer or gas for generating plasma.

It is effective that at least one part of the supply line of gas introduced to the inductively coupled plasma mass spectrometer or gas for generating plasma constitutes a part of the line before the connection point with the gas supply line leading from the outlet of the gas chromatograph.

In the present disclosure where conditions and/or structure are not specified, the skilled artisan in the art can readily provide such conditions and/or structure, in view of the present disclosure, as a matter of routine experimentation.

Embodiments of the present invention are explained in details below by using the attached drawings.

Figure 1B:
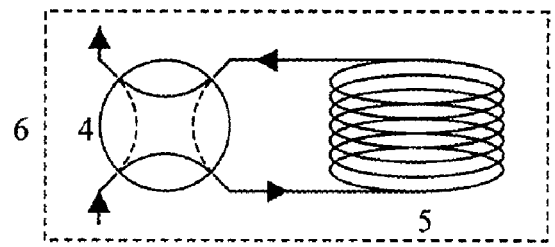
FIG. 1(b) is a drawing showing a condition after switching the four-way selector valve in FIG. 1(a).

FIG. 1 (a) is a drawing showing an embodiment of an analyzer constituted by gas chromatograph combined with inductively coupled plasma mass spectrometer conforming to the present invention.

FIG. 1 (b) is a drawing showing a condition after switching the four-way selector valve in FIG. 1 (a).

In FIG. 1 (a), an oxygen introduction unit 6 comprising a selector valve 4 and an oxygen permeable tube 5 is installed in a makeup gas supply line 1, which is one of the three gas lines supplying argon to plasma.

In terms of the effect of suppressing carbon deposition, it is most effective that this oxygen introduction unit 6 is installed in the makeup gas supply line 1.

Depending on the condition, however, the unit can also be installed in an auxiliary gas supply line 2 or a plasma gas supply line 3.

Target components of analysis (such as 7, 8, 9) are introduced to an injection port 12 of a gas chromatograph (GC) 11 in a state dissolved in a solvent 10, after which they are transported by the carrier gas, separated in a column 13, and travel through an inactivation column 15 installed in a heating transfer chamber 14 to be introduced to plasma (ICP) 16. In FIG. 1 (a), the inactivation column 15 penetrates through a heating transfer tube 14 to a point in the immediate vicinity of plasma 16. In addition to this configuration, it is also possible to use a configuration where only a part of the inactivation column 15, after the connection point with a connector 22, penetrates into the heating transfer tube 14.

Here, the target components of analysis 7, 8, 9 are separated from each other and also from the solvent 10 before being introduced to ICP.

On the other hand, argon (Ar) used as the makeup gas is supplied from an Ar cylinder 17, travels through a mass flow controller 18 that controls the flow rate of the gas, enters a pre-heater 21 of the GC after traveling along the route in the selector valve indicated by solid lines, and finally enters ICP 16 by traveling through the connector 22 and heating transfer tube 14.

In this condition, the makeup gas is not flowing through the oxygen permeable tube 5 and therefore oxygen is not supplied to ICP.

When the selector valve is switched to the condition shown in FIG. 1 (b), the Ar makeup gas flows through the oxygen permeable tube 5 and is mixed with the oxygen that has permeated through the permeable tube, after which the mixture gas is introduced to ICP 16. (This corresponds to Embodiment 2).)

To introduce oxygen continuously, the valve is kept in the condition in FIG. 1 (b). To introduce oxygen during a specific period, such as only during the period in which the solvent 10 is introduced to ICP, the valve is kept in the condition in FIG. 1 (b) only during the applicable period and kept in the condition in FIG. 1 (a) during all other periods.

It is effective that the aforementioned selector valve switching is implemented synchronously with the solvent signals from the ICP-MS. This can be achieved by using an automatic control unit 23. To be specific, a trigger signal is output from the ICP-MS to the automatic control unit 23 when the signal intensity attributable to the solvent exceeds a specific level, and a trigger signal is output again when the signal intensity drops to or below the specific level, so that the selector valve is switched and oxygen is introduced only during the period between the trigger signals.

The organic solvent is decomposed in the high-temperature argon ICP. In a condition where no oxygen is available, the solvent deposits as carbon around the orifices of a sampling cone 24 and a skimmer cone 25. In a condition where ample oxygen is available, on the other hand, the solvent becomes CO or $CO_2$ and does not deposit.

The amount of oxygen required in this reaction need not be controlled strictly, and any amount is sufficient as long as sufficient oxidation reaction takes place in a manner not affecting the stability of ICP.

For the oxygen permeable tube, a silicone tube, Teflon® AF tube (Teflon is a registered trademark of DuPont) or mixed conductive oxygen permeable tube can be used, among others. Needless to say, other tubes providing higher oxygen permeability can also be used.

Figure 2:
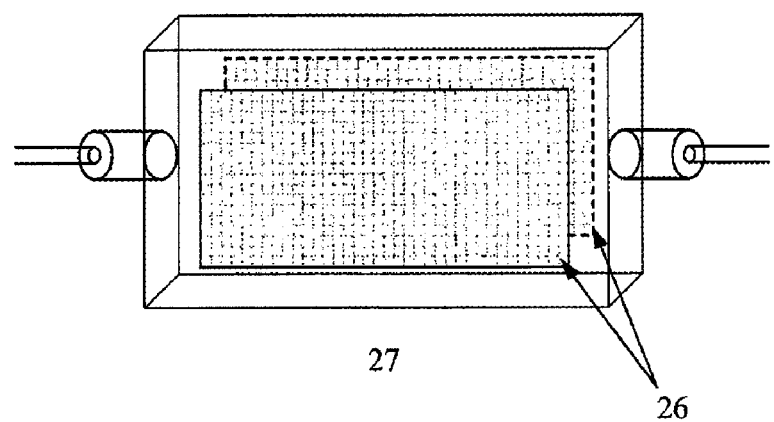
FIG. 2 is a drawing showing an oxygen permeation module that uses an oxygen permeable membrane.

The amount of oxygen permeation can be adjusted to a required level by changing the outer diameter (e.g., 0.5-3 mm), thickness (e.g., 0.025-0.3 mm) or length (e.g., 5-100 cm) of the tube or number of tubes (e.g., 1-50 tubes). In the above, it is important to enable sufficient oxygen to be supplied to the extent that plasma is not extinguished. The required amount of oxygen also depends on the amount of a sample to be supplied. In an embodiment, the amount of a sample to be supplied is approximately 1 µL, but in another embodiment, the amount may be as large as 5 µL, or in the case of a packed column, a maximum amount of a sample to be supplied may reach 30 µL. In the above embodiments, a large quantity of oxygen may be required, and accordingly, the length of a tube needs to be long, the thickness of a tube needs to be thin, and/or the outer diameter of a tube needs to be large. These three parameters are mutually related to each other, and thus, if the outer diameter of a tube is relatively small, the length of the tube needs to be relatively long for a trade-off. This adjustment can also be made by means of controlling the temperature (e.g., 10-60° C.) of air contacting the oxygen permeable tube. It is also possible to install an oxygen permeable module 27 partially using an oxygen permeable membrane 26, like the one shown in FIG. 2, instead of the oxygen permeable tube, in a part of the gas line that supplies argon to plasma. (This corresponds to Embodiment 1).)

Such oxygen permeable tube or oxygen permeable membrane need not have the property of permeating only oxygen, and any tube or membrane that also permeates nitrogen, carbon dioxide or any other gas along with oxygen can also be used as long as the stability of ICP is not affected.

When the valve is switched and a large amount of oxygen is introduced at once through the oxygen permeable tube, sometimes ICP disappears. From the viewpoint of measurement, it is effective to prevent this disappearance of ICP occurring as a result of introduction of a large amount of oxygen at once. Among the methods to prevent introduction of a large amount of oxygen at once, one effective means is to use an oxygen permeable tube having a double-tube structure comprising an outer tube constituted by a Teflon® AF tube as described above and an inner tube constituted by a nylon tube that virtually permeates no oxygen, and fill the tube having the above structure by closing its two ends.

Observation of signal spikes reveals that they become considerably small immediately after switching. This indicates that only a small amount of $O_2$ had permeated from air into the tube and accumulated before the valve was switched. In other words, the inner tube that does not permeate $O_2$ limits the volume of accumulated $O_2$ to a level corresponding to the space between the inner tube and outer tube, which in turns reduces the amount of $O_2$ introduced to ICP. As can be easily deduced from the above example, the inner tube need not be a hollow tube, and a solid tube whose interior space is filled can also be used.

In preventing introduction of a large amount of oxygen at once, it is also an effective means to use a Teflon® AF tube and connect to this tube, as a buffer, a glass tube filled with quartz wool to mitigate abrupt change in gas after the four-way selector valve. Effectiveness of this means is substantiated by the fact that it can also achieve gradual change in signal spikes immediately after switching.

In the present disclosure where conditions and/or structures are not specified, the skilled artisan in the art can readily provide such conditions and/or structures, in view of the present disclosure, as a matter of routine experimentation.

Embodiments of the present invention are explained in greater details below by using more specific examples.

EXAMPLE 1

In the system shown in FIG. 1, a Teflon® AF tube (Teflon is a registered trademark of DuPont) (outer diameter 1 mm, inner diameter 0.8 mm, length 10 cm) was used as the oxygen permeable tube 5. Both ends of the tube were connected to a four-way selector valve. The exterior surface of this tube was exposed to air, and the system was used in room temperature. The flow rate of makeup gas was adjusted to 1.05 L/min. This system was used to observe an increase/decrease in the amount of carbon depositing on the sampling cone in conditions where oxygen was introduced and not introduced. The outer and inner diameters and the length of the tube should not be limited to the above and can be selected according to the configuration of a system, etc. (e.g., the tube may have a length of 20 cm or longer).

Since the carbon deposit on the sampling cone illuminates in orange, increase/decrease in carbon can be visually observed.

When 1 µL of solvent hexane was introduced to the gas chromatograph as a sample, the deposited carbon remained after 10 minutes of hexane introduction if oxygen was not introduced (i.e., the four-way selector valve was in the condition in FIG. 1 (a)). When oxygen was introduced (i.e., the four-way selector valve was in the condition in FIG. 1 (b)), the carbon deposit was removed completely within approx. 1 minute of hexane introduction.

Figure 3A:
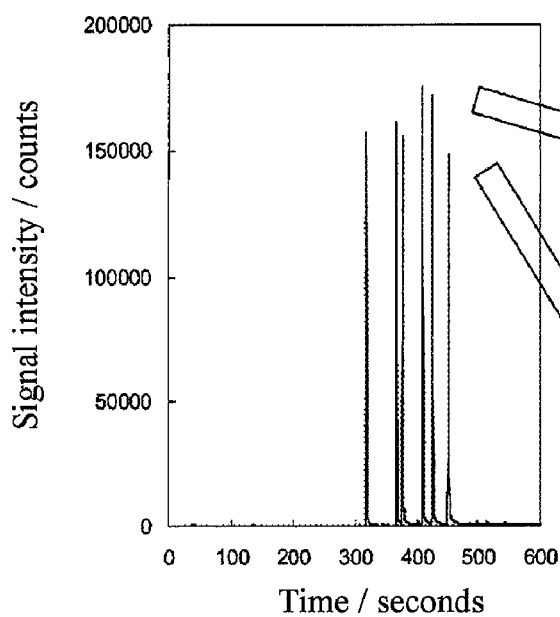
FIG. 3(a) is a chromatogram showing the analysis results after the first introduction of a hexane solution of polybromodiphenyl ether without oxygen introduction.
Figure 3B:
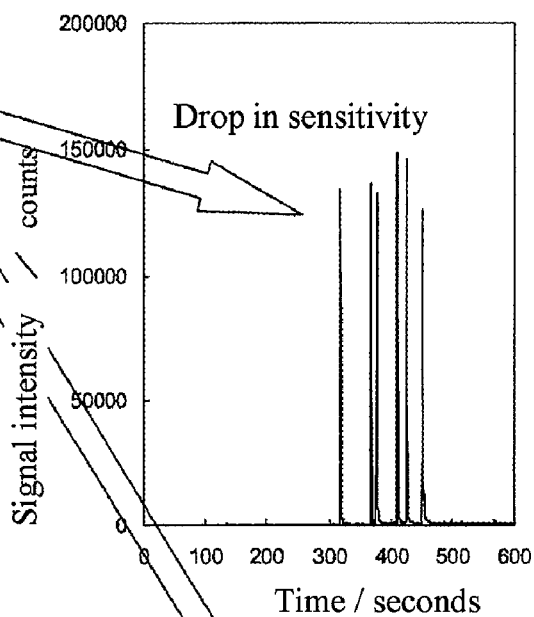
FIG. 3(b) is a chromatograph showing the analysis results after ten continuous introductions of the solution without oxygen introduction.
Figure 3C:
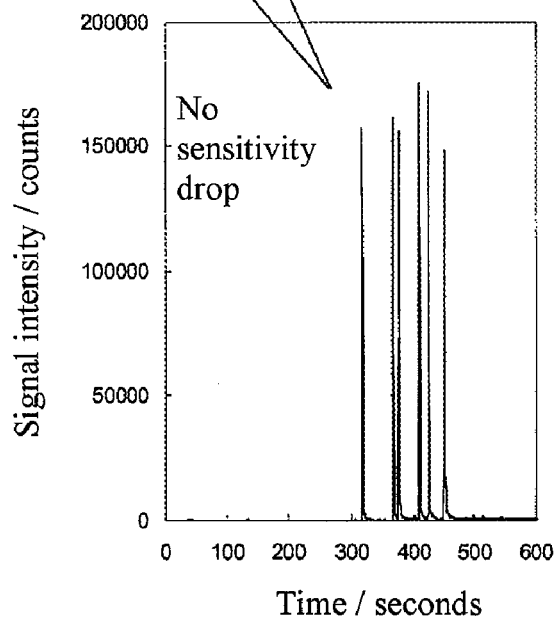
FIG. 3(c) is a chromatogram showing the analysis results after ten continuous introductions of the solution with oxygen introduction.

FIG. 3 shows chromatograms taken after the first and tenth introductions, among ten continuous introductions, of 1 µL of the target component of analysis prepared by dissolving in solvent hexane a polybromodiphenyl ether (constituted by six isomers with the concentration of each isomer adjusted to 400 ng/mL) used in brominated flame retardants. Here, FIG. 3 (a) is a chromatogram taken after the first introduction. FIG. 3 (b) is a chromatograph taken after ten continuous introductions made in a condition where makeup gas was not flowing through the Teflon AF tube and therefore oxygen was not introduced, while FIG. 3 (c) is a chromatograph taken after ten continuous introductions made in a condition where makeup gas was flowing through the Teflon AF tube and therefore oxygen was introduced. As evident from these chromatograms, while the sensitivity dropped by approx. 20% when oxygen was not introduced, carbon deposition was suppressed and sensitivity drop was prevented when oxygen was introduced through the oxygen permeable tube.

EXAMPLE 2

Figure 4:
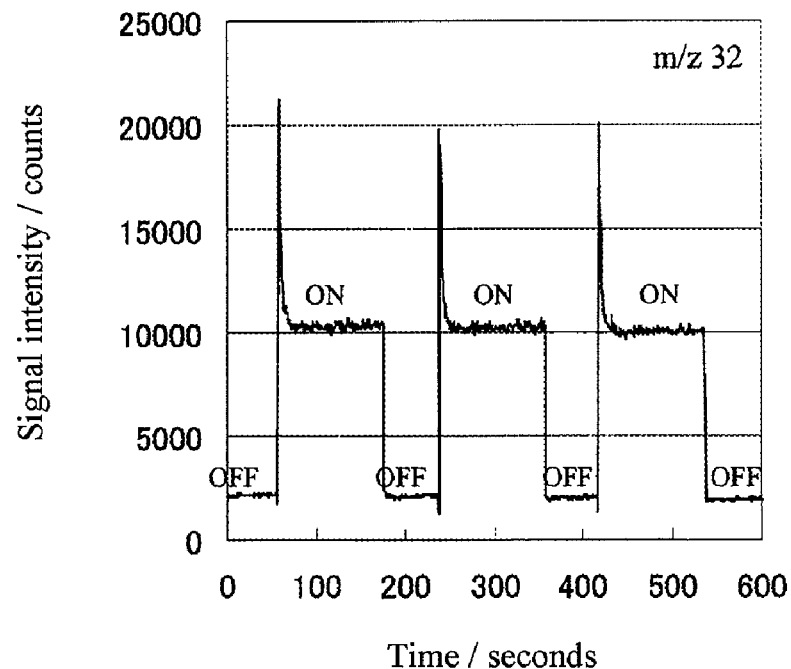
FIG. 4 is a drawing showing the change in signal intensity at a mass/charge number (m/z) value of 32 when the four-way selector valve was switched at specific intervals (Example 2).

By using as the oxygen permeable tube 5 the same Teflon® AF tube (outer diameter 1 mm, inner diameter 0.8 mm, length 10 cm) employed in Example 1, the four-way selector valve was switched at specific intervals and signal intensity was measured at a mass/charge number (m/z) value of 32. The flow rate of makeup gas was adjusted to 1.05 L/min. The results are shown in FIG. 4. When the valve was switched to let argon makeup gas flow through the oxygen permeable tube ("ON" condition in FIG. 4), the signal intensity at m/z 32 increased to a constant level. This indicates that oxygen gas ($O_2$, mass 32) was introduced to ICP. The signal spike immediately after switching reflects the introduction to ICP of $O_2$ in air that had permeated through and accumulated in the tube before the valve was switched, and the subsequent stabilization of signal intensity indicates that the amount of $O_2$ permeating through the oxygen permeable tube became constant. When the valve was switched to prevent argon makeup gas from flowing through the oxygen permeable tube ("OFF" condition in FIG. 4), the signal intensity at m/z 32 dropped to a constant level within 2 seconds. This shows that oxygen can be introduced for a specific period only. In particular, the fact that the signal intensity returned to the original low level within a short period of only 2 seconds is important in applications where measurement must be conducted at m/z 32, as is the case of measuring sulfur compounds in petroleum. In these applications, background signals remain high when the signal intensity does not return to the original low level, resulting in a rise in the lower detection limit. The system proposed in the present application for patent allows $O_2$ to be introduced only during the period in which the organic solvent is introduced, while stopping $O_2$ introduction in all other periods, with great ease by simply switching the valve. Accordingly, this system simultaneously satisfies the two requirements of preventing carbon deposition and reducing background signals.

EXAMPLE 3

Figure 5:
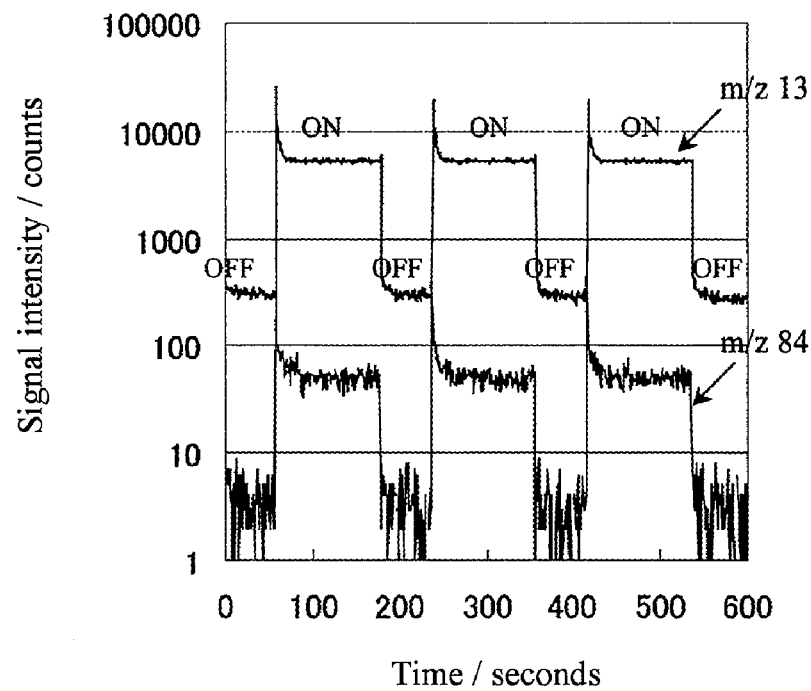
FIG. 5 is a drawing showing the change in signal intensity at mass/charge number (m/z) values of 13 and 84 when the four-way selector valve was switched at specific intervals (Example 3).

By using as the oxygen permeable tube 5 the same Teflon® AF tube (outer diameter 1 mm, inner diameter 0.8 mm, length 10 cm) employed in Example 1, the four-way selector valve was switched at specific intervals and signal intensity was measured at mass/charge number (m/z) values of 13 and 84. The flow rate of makeup gas was adjusted to 1.05 L/min. The results are shown in FIG. 5. When the valve was switched to let argon makeup gas flow through the oxygen permeable tube ("ON" condition in FIG. 5), the signal intensity increased to a constant level both at m/z 13 and 84. This indicates that $CO_2$ and Kr in air permeated through the oxygen permeable tube and entered ICP, thereby causing $^{13}C$ and $^{84}Kr$ to be detected. The notable difference between the signal intensities of the two is explained by the different abundances in air (approx. 370 ppm for $CO_2$ and approx. 1.1 ppm for Kr) and different membrane permeabilities. The above results indicate that this system not only suppresses carbon deposition by introducing $O_2$ to ICP, but it also enables GC/ICP-MS measurement of gas components in air by allowing the components to permeate through the membrane. Since the amount of permeated gas is proportional to the partial pressure of gas, of course the concentration of gas can be quantified. In addition to supporting the inorganic gases mentioned above, it was also possible to measure volatile organic compounds (VOCs) by measuring $^{13}C$, and volatile organic chlorine compounds by measuring $^{35}Cl$ or $^{37}Cl$.

EXAMPLE 4

Figure 6:
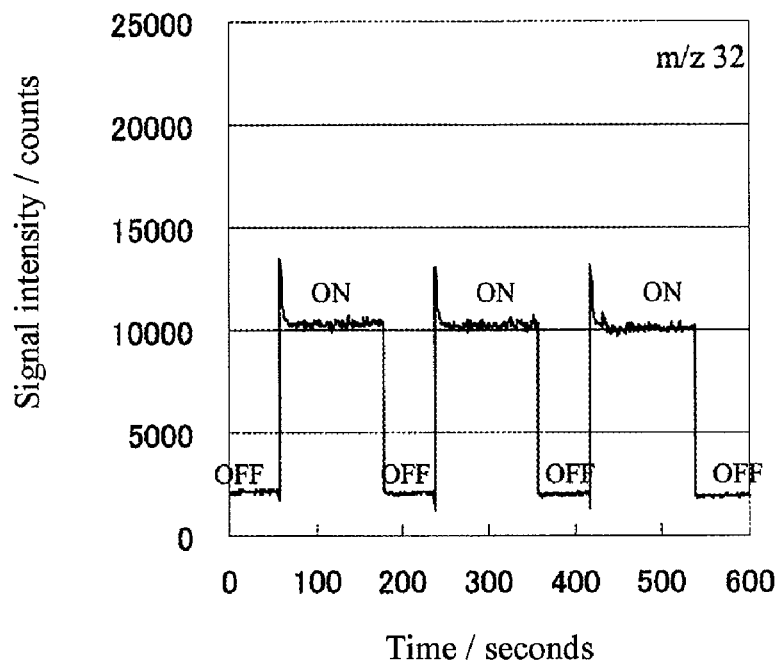
FIG. 6 is a drawing showing the change in signal intensity at a mass/charge number (m/z) value of 32 when the four-way selector valve was switched at specific intervals (Example 4).

As the oxygen permeable tube 5, a tube of double-tube structure comprising an outer tube constituted by the same Teflon® AF tube employed in Example 1 (outer diameter 1 mm, inner diameter 0.8 mm, length 10 cm) and an inner diameter constituted by a nylon tube permeating virtually no oxygen (outer diameter 0.6 mm, inner diameter 0.4 mm, length 10 cm; both ends were closed) was used. The four-way selector valve was switched at specific intervals and signal intensity was measured at a mass/charge number (m/z) value of 32. The flow rate of makeup gas was adjusted to 1.05 L/min. The results are shown in FIG. 6. When the valve was switched to let argon makeup gas flow through the oxygen permeable tube ("ON" condition in FIG. 6), the signal intensity at m/z 32 increased to a constant level, but the signal spikes immediately after switching were significantly smaller than those shown in FIG. 4. This indicates that only a small amount of $O_2$ had permeated from air into the tube and accumulated before the valve was switched. To be specific, the inner tube not permeating $O_2$ limited the volume of accumulated $O_2$ to a level corresponding to the space between the inner tube and outer tube, which in turns reduced the amount of $O_2$ introduced to ICP. Sometimes ICP disappears when a large amount of oxygen is introduced at once. Use of a tube having the above structure reduces the probability of this ICP disappearance. The subsequent signal intensities are roughly the same as those shown in FIG. 4, because the surface area of the outer oxygen permeable tube contacting air does not change in the double-tube structure. As can be easily deduced from the above example, the inner tube need not be a hollow tube, and a solid tube whose interior space is filled can also be used.

EXAMPLE 5

Figure 7:
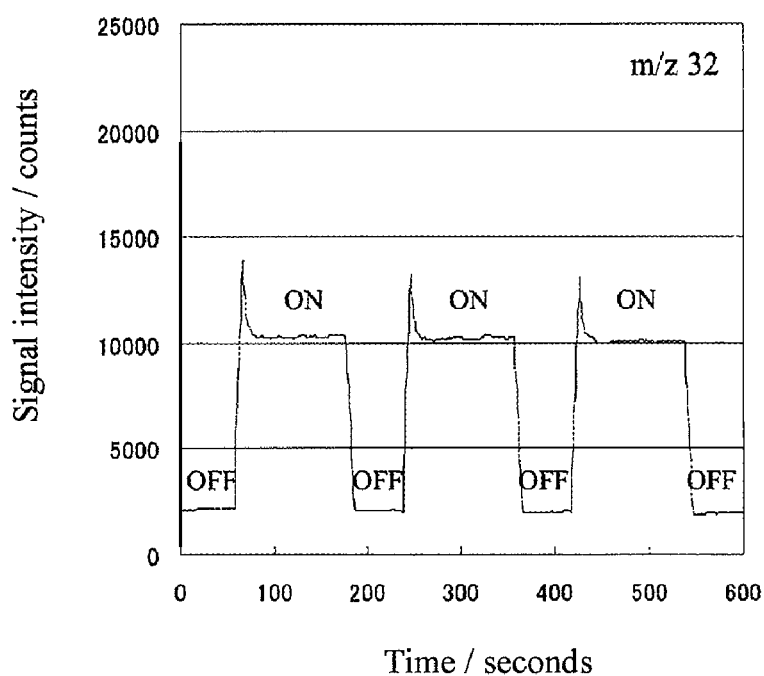
FIG. 7 is a drawing showing the change in signal intensity at a mass/charge number (m/z) value of 32 when the four-way selector valve was switched at specific intervals (Example 5).

By using as the oxygen permeable tube 5 the same Teflon® AF tube (outer diameter 1 mm, inner diameter 0.8 mm, length 10 cm) employed in Example 1, and connecting a 10-mL glass tube (buffer) filled with quartz wool after the four-way selector valve, the four-way selector valve was switched at specific intervals and signal intensity was measured at a mass/charge number (m/z) value of 32. The flow rate of makeup gas was adjusted to 1.05 L/min. The results are shown in FIG. 7. When the valve was switched to let argon makeup gas flow through the oxygen permeable tube ("ON" condition in FIG. 7), the signal intensity at m/z 32 increased to a constant level, but the changes in signal spikes immediately after switching were more gradual than those shown in FIG. 4. This indicates that the amount of $O_2$ that had permeated through and accumulated in the tube before the valve was switched was mixed with and diluted by argon gas in the glass tube filled with quartz wool, thereby causing a gradual change in the concentration of $O_2$ introduced to ICP. In other words, although the absolute amount of $O_2$ introduced to ICP remained the same, $O_2$ was introduced to ICP over a longer period of time and therefore the probability of ICP disappearance was reduced. While it took a longer time to reach a specific level of signal intensity, the signal intensity after replacement of argon in the buffer was roughly the same as the level shown in FIG. 4.

Although all possible variations are not listed herein, the present invention can be embodied in any modes incorporating various changes, modifications and improvements based on the knowledge of those skilled in the art. It goes without saying that these embodiments are also included in the scope of the present invention, as long as they do not deviate from the purpose of the present invention. Therefore, it should be clearly understood that the forms of the present invention are illustrative only and are not intended to limit the scope of the present invention.

The present application claims priority to Japanese Patent Application No. JP2006-239897, filed Sep. 5, 2006, and No. JP2007-213260, filed Aug. 20, 2007, the disclosure of which is incorporated herein by reference in its entirety.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. An analyzer constituted by a gas chromatograph combined with an inductively coupled plasma mass spectrometer, comprising an oxygen permeable tube or oxygen permeable membrane in at least one part of a supply line of gas introduced to the inductively coupled plasma mass spectrometer or gas for generating plasma, wherein oxygen in air outside the supply line can be taken in through the oxygen permeable tube or oxygen permeable membrane according to the difference in partial pressure of oxygen and introduced to the supply line.

2. The analyzer constituted by the gas chromatograph combined with the inductively coupled plasma mass spectrometer according to claim 1, wherein the at least one part of the supply line of gas introduced to the inductively coupled plasma mass spectrometer or gas for generating plasma constitutes a part of the line before the connection point with the gas supply line leading from the outlet of the gas chromatograph.

3. The analyzer constituted by the gas chromatograph combined with the inductively coupled plasma mass spectrometer according to claim 2, wherein the at least one part of the supply line of gas introduced to the inductively coupled plasma mass spectrometer or gas for generating plasma constitutes a part of the line before the connection point with the gas supply line leading from the outlet of the gas chromatograph, and this part of the line has a selector valve installed at the location connecting the front and rear sections of the line and having an oxygen permeable tube or oxygen permeable membrane, so that when the selector valve is switched, oxygen can be introduced during a desired period through the location having the oxygen permeable tube or oxygen permeable membrane.

4. The analyzer constituted by the gas chromatograph combined with the inductively coupled plasma mass spectrometer according to claim 3, wherein the oxygen permeable tube has a double-tube structure comprising an outer tube constituted by an oxygen permeable tube and an inner tube constituted by an oxygen impermeable tube.

5. The analyzer constituted by the gas chromatograph combined with the inductively coupled plasma mass spectrometer according to claim 2, wherein the oxygen permeable tube has a double-tube structure comprising an outer tube constituted by an oxygen permeable tube and an inner tube constituted by an oxygen impermeable tube.

6. The analyzer constituted by the gas chromatograph combined with the inductively coupled plasma mass spectrometer according to claim 1, wherein the at least one part of the supply line of gas introduced to the inductively coupled plasma mass spectrometer or gas for generating plasma constitutes a part of the line before the connection point with the gas supply line leading from the outlet of the gas chromatograph, and this part of the line has a selector valve installed at the location connecting the front and rear sections of the line and having an oxygen permeable tube or oxygen permeable membrane, so that when the selector valve is switched, oxygen can be introduced during a desired period through the location having the oxygen permeable tube or oxygen permeable membrane.

7. The analyzer constituted by the gas chromatograph combined with the inductively coupled plasma mass spectrometer according to claim 6, further comprising an automatic control unit that switches the selector valve using electrical signals.

8. The analyzer constituted by the gas chromatograph combined with the inductively coupled plasma mass spectrometer according to claim 7, wherein a trigger signal is output from the inductively coupled plasma mass spectrometer to the automatic control unit when the signal intensity attributable to a solvent exceeds a specific level, and a trigger signal is output again when the signal intensity drops to or below the specific level, and the selector valve is switched.

9. The analyzer constituted by the gas chromatograph combined with the inductively coupled plasma mass spectrometer according to claim 8, wherein the oxygen permeable tube has a double-tube structure comprising an outer tube constituted by an oxygen permeable tube and an inner tube constituted by an oxygen impermeable tube.

10. The analyzer constituted by the gas chromatograph combined with the inductively coupled plasma mass spectrometer according to claim 8, wherein a buffer for mitigating abrupt rise in the oxygen content of oxygen gas is provided in a part of the gas supply line between the selector valve and a plasma torch.

11. The analyzer constituted by the gas chromatograph combined with the inductively coupled plasma mass spectrometer according to claim 7, wherein the oxygen permeable tube has a double-tube structure comprising an outer tube constituted by an oxygen permeable tube and an inner tube constituted by an oxygen impermeable tube.

12. The analyzer constituted by the gas chromatograph combined with the inductively coupled plasma mass spectrometer according to claim 7, wherein a buffer for mitigating abrupt rise in the oxygen content of oxygen gas is provided in a part of the gas supply line between the selector valve and a plasma torch.

13. The analyzer constituted by the gas chromatograph combined with the inductively coupled plasma mass spectrometer according to claim 6, wherein a buffer for mitigating abrupt rise in the oxygen content of oxygen gas is provided in a part of the gas supply line between the selector valve and a plasma torch.

14. The analyzer constituted by the gas chromatograph combined with the inductively coupled plasma mass spectrometer according to claim 1, wherein the oxygen permeable tube has a double-tube structure comprising an outer tube constituted by an oxygen permeable tube and an inner tube constituted by an oxygen impermeable tube.

15. The analyzer constituted by the gas chromatograph combined with the inductively coupled plasma mass spectrometer according to claim 14, wherein a buffer for mitigating abrupt rise in the oxygen content of oxygen gas is provided in a part of the gas supply line between the selector valve and a plasma torch.

16. An analyzer comprising a gas chromatograph and an inductively coupled plasma mass spectrometer disposed downstream of the gas chromatograph, said analyzer having a supply line of gas introduced to the inductively coupled plasma mass spectrometer or gas for generating plasma in the inductively coupled plasma mass spectrometer, wherein at least one part of the supply line is oxygen-permeable, wherein oxygen in air outside the supply line can be taken in through the oxygen permeable tube or oxygen permeable membrane according to the difference in partial pressure of oxygen and introduced to the supply line.

17. The analyzer according to claim 16, wherein the oxygen-permeable supply line is constituted by an oxygen-permeable tub or membrane.

18. The analyzer according to claim 17, wherein the oxygen-permeable supply line is an oxygen permeable tube having a double-tube structure comprising an oxygen-permeable outer tube and an oxygen impermeable inner tube, wherein the gas is to flow between the outer and inner tubes.

19. The analyzer according to claim 16, wherein the supply line of gas is comprised of a downstream supply line and an upstream supply line connected to the downstream supply line, said downstream supply line extending out of the gas chromatograph and connected to the inductively coupled plasma mass spectrometer, said upstream supply line connected to the gas chromatograph and joined to the downstream supply line in the gas chromatograph, wherein the oxygen-permeable supply line is a part of the upstream supply line.

20. The analyzer according to claim 19, wherein the upstream supply line has two paths provided with a selector valve for switching the paths at a given time period, said two paths being constituted by one path including the oxygen-permeable supply line and the other path including no oxygen-permeable supply line.

21. The analyzer according to claim 20, wherein the selector valve is structured to switch the paths to the oxygen-permeable supply line when the intensity of a signal indicative of a solvent introduced in the gas chromatograph, which signal is transmitted from the inductively coupled mass spectrometer, exceeds a give level.

22. The analyzer according to claim 20, wherein a buffer for mitigating an abrupt rise of oxygen content in the gas is provided in the supply line downstream of the selector valve.

* * * * *